US012577515B2

(12) United States Patent
Levin et al.

(10) Patent No.: US 12,577,515 B2
(45) Date of Patent: Mar. 17, 2026

(54) PHOTOBIOREACTOR

(71) Applicants: Alexander Levin, Binyamina (IL);
Hanan-Emanuel Levin, Binyamina
(IL)

(72) Inventors: Alexander Levin, Binyamina (IL);
Hanan-Emanuel Levin, Binyamina
(IL)

( * ) Notice: Subject to any disclaimer, the term of this
patent is extended or adjusted under 35
U.S.C. 154(b) by 0 days.

(21) Appl. No.: 18/324,204

(22) Filed: May 26, 2023

(65) Prior Publication Data

US 2024/0392221 A1 Nov. 28, 2024

(51) Int. Cl.
C12M 1/00 (2006.01)

(52) U.S. Cl.
CPC ............ C12M 21/02 (2013.01); C12M 23/26
(2013.01); C12M 29/24 (2013.01)

(58) Field of Classification Search
CPC ....... C12M 21/02; C12M 23/26; C12M 29/24
See application file for complete search history.

(56) References Cited

U.S. PATENT DOCUMENTS

| | | | |
|---|---|---|---|
| 3,468,057 A | 9/1969 | Buisson et al. | |
| 3,955,317 A | 5/1976 | Gudin | |
| 3,998,186 A | 12/1976 | Hodges | |
| 4,084,346 A | 4/1978 | Stengel et al. | |
| 4,360,005 A * | 11/1982 | Sharpe | F24S 80/525 |
| | | | 126/599 |
| 5,443,985 A | 8/1995 | Lu et al. | |

| | | | |
|---|---|---|---|
| 5,534,417 A | 7/1996 | Arad et al. | |
| 5,741,702 A | 4/1998 | Lorenz | |
| 5,846,816 A | 12/1998 | Forth | |
| 5,981,271 A | 11/1999 | Doucha et al. | |
| 5,992,508 A * | 11/1999 | Lowenstein | F28F 3/14 |
| | | | 165/905 |
| 6,827,036 B2 | 12/2004 | Connolly | |
| 8,110,395 B2 | 2/2012 | Lewnard et al. | |
| 8,245,440 B2 | 8/2012 | Ryan | |
| 8,318,478 B2 | 11/2012 | Dahle | |
| 8,361,786 B2 | 1/2013 | Hu et al. | |
| 8,658,420 B2 | 2/2014 | Gorny et al. | |
| 8,986,985 B2 * | 3/2015 | Levin | C12M 23/38 |
| | | | 435/305.3 |

(Continued)

OTHER PUBLICATIONS

Hu, Q., Zhang, C., Lee, Y.K., "Flat Inclined Modular Photobioreactor," Biotechnol. Bioeng., 1996, 51(1):51-60, Wiley, Hoboken, NJ, USA.

(Continued)

*Primary Examiner* — William H. Beisner
*Assistant Examiner* — Danielle B Henkel

(57) ABSTRACT

The invention discloses a photobioreactor featuring a microalgae cultivation chamber in the form of a closed flat duct irradiated by sunlight. The flat duct is constructed from an inflatable sleeve made of transparent polymer film. This inflatable sleeve is sandwiched between a bank of frames with wire nettings, plates of foamed plastic, a variable air pressure mattress located underneath the inflatable sleeve, and a thermo-insulating transparent inflatable mattress and glass panes above. The variable air pressure mattress facilitates mixing of the microalgae suspension with the gaseous medium containing carbon dioxide and regulates the temperature of the microalgae suspension in the flat duct.

15 Claims, 13 Drawing Sheets

(56) References Cited

U.S. PATENT DOCUMENTS

| | | | |
|---|---|---|---|
| 9,938,492 B2 | 4/2018 | Gressel et al. | |
| 10,906,797 B2 | 2/2021 | Levin | |
| 11,034,924 B2 * | 6/2021 | Levin | C12M 1/002 |
| 2007/0048848 A1 * | 3/2007 | Sears | C12N 1/12 |
| | | | 554/174 |
| 2007/0155006 A1 * | 7/2007 | Levin | C12M 31/08 |
| | | | 47/1.4 |
| 2009/0011492 A1 | 1/2009 | Berzin | |
| 2009/0130706 A1 | 5/2009 | Berzin et al. | |
| 2010/0028976 A1 | 2/2010 | Hu et al. | |
| 2011/0217692 A1 * | 9/2011 | Morgan | C12M 23/04 |
| | | | 435/292.1 |
| 2011/0258920 A1 | 10/2011 | Licamele et al. | |
| 2011/0300624 A1 | 12/2011 | Lim | |
| 2014/0099685 A1 * | 4/2014 | Tuttman | C12M 21/02 |
| | | | 435/157 |
| 2014/0242681 A1 | 8/2014 | Fiorentino | |
| 2015/0275161 A1 * | 10/2015 | Gressel | C12M 23/06 |
| | | | 435/257.1 |
| 2016/0130546 A1 | 5/2016 | Leimbach | |
| 2020/0024558 A1 * | 1/2020 | Levin | C12M 29/12 |
| 2021/0062124 A1 | 3/2021 | Olaizola et al. | |

OTHER PUBLICATIONS

Posten, C., "Design Principles of Photo-Bioreactors," Eng. Life Sci., 2009, 9(3):165-177, Wiley-VCH, Weinheim, Germany.

Pulz, O., "Photobioreactors: Prod. Systems for Microorganisms," Appl. Microbiol. Biotechnol., 2001, 57(3):287-293, Springer, Berlin, Germany.

Pawlita-Posmyk, M. et al., "Influence of Temp on Algal Biomass," MATEC Web Conf., 2018, 240:04008, EDP Sciences, Les Ulis, France.

Ras, M. et al., "Temp Effect on Microalgae," HAL Archive, 2013, Id: hal-00852286, INRAE, Paris, France.

* cited by examiner

PHOTOBIOREACTOR

BACKGROUND OF THE INVENTION

This invention relates to the field of bioreactors for cultivation of microalgae or cyanobacteria.

Mass cultivation of microalgae or cyanobacteria has great potential for modern agriculture, biochemistry and pharmaceutics.

Algal species: *Spirulina, Dunaliella* and others present important sources of vitamins, proteins, unsaturated fats, organic compounds of iron and other microelements. The most common forms of microalgae or cyanobacteria cultivation photobioreactors are open ponds or open raceways channels.

There are some technical problems connected with the application of such systems:

a) Light distribution within photobioreactors constructed as ponds or channels presents a serious problem. The depth of the pond or raceway channels should be in the range of 15/30 cm.

It determines in turn relatively low final microalgae (or cyanobacteria) concentration in nutritious solution and high cost of harvesting microalgae biomass.

b) Mixing the nutritious solution in order to prevent cell sinking, and, in addition, to remove from the nutritious solution the generated oxygen, which inhibits photosynthesis process.

c) It is necessary to provide an adequate amount of $CO_2$, which is required for performance of photosynthesis process; this $CO_2$ is supplied as a rule from the ambient air or from gaseous medium enriched with $CO_2$ by its dissolution in the nutritious solution.

d) Maintenance of optimum ranges of daily and nightly temperatures of the nutritious solutions.

There are patents and patent applications, which are devoted to solving a part of the above-mentioned problems; however, these patents and patent applications do not provide sufficiently effective and cheap solutions to the described problems.

U.S. Pat. No. 4,084,346 describes a system of channels intended for algae growing; there are discharge means installed in these channels which introduce $CO_2$, into the microalgae suspension.

U.S. Pat. No. 3,468,057 describes a basin for the culture of algae in an aqueous nutrient medium comprising, in combination, at least two illuminated horizontal zones, at least two inclined zones and at least one gas injection means.

U.S. Pat. No. 3,955,317 describes a method for growing plant cells containing chloroplasts in liquid suspension simultaneously with the growth of photosynthetic bacteria, in which method the liquid suspension containing the plant cells is enclosed in a first elongated, at least partially transparent, container and a liquid suspension of photosynthetic bacteria is contained in second elongated, at least partially transparent, container, the said second container is attached to the said first container so that light passing through the said first container then passes through the said second container; the said containers preventing passage of liquid from one container to the other, the containers being supported on a body of water; the liquid suspension in the first container being exposed to light and brought into contact with carbon dioxide.

U.S. Pat. No. 3,998,186 describes a method and apparatus for shrimp culture; shrimp hatched and brought through larval and post-larval stages environment unit which includes plastic cover means positioned over an elongated waterway containing seawater, or the like, and algae in substantial amounts. The design of the unit and the technique of intermittently supplying seawater allows the control of light intensity and light spectral characteristics within the shrimp growing area and the control of seawater flow rate, temperature and dissolved oxygen content of the seawater in the waterway.

U.S. Pat. No. 5,443,985 describes a bioreactor for culturing living cells, particularly shear-sensitive cells, wherein the bioreactor is composed of a stationary vessel with opposite-spaced walls inclined at an angle to form upper and lower walls. Liquid culture medium and cell culture, such as hybridoma cells, are introduced into the vessel and gas is introduced at the lower end of the vessel to form gas bubbles which travel upward along the upper wall of the bioreactor to disengage from a small portion of the gas-liquid interface. The gas bubbles circulate the cells and liquid medium, maintaining the cells in suspension and lifting them in a circulating path upwardly parallel to the upper wall and downward along the lower wall. The bioreactor design thus achieves bulk mixing and aeration by maintaining a significant degree of segregation between the upwardly traveling bubbles and the cells in the liquid medium avoiding unnecessary cell damage by fluid-mechanical shear or by bubble bursting events.

U.S. Pat. No. 5,534,417 describes a method of growing microalgae, which uses outdoor sunlight as a source of energy. Growth is confined to an assembly of vertical, transparent tubes through which nutrients and air are carried with carbon dioxide. The microalgae are periodically harvested from the tubes.

U.S. Pat. No. 5,741,702 describes a reactor vessel for processing gases containing carbon dioxide using a fluid containing algae; this reactor vessel comprises: a first elongated duct having a rectangular cross-section with a top surface and a bottom surface for containing said gases and said fluid containing algae; a second elongated duct, abutting said first elongated duct, having a rectangular cross-section with a top surface and a bottom surface, said duct having ribs extending from said bottom surface to said top surface to form a plurality of elongated channels for insulating said first elongated duct; wherein the channels of said second elongated duct is constructed to be evacuated to create a vacuum therein.

U.S. Pat. No. 5,846,816 describes a bioreactor for biomass production comprising: a substantially transparent chamber, the chamber being at least suitable for containing biomass in a liquid phase, and having a base portion, an upper portion, and several side walls between the base portion and the upper portion, the side walls being configured to generally diverge from the base portion towards the wider upper portion; and circulating means for circulating the contents of the chamber, wherein the circulating means creates a motive force within the liquid phase sufficient to ensure continual mixing of substantially all of the biomass and at least cyclical exposure of biomass to a light source.

U.S. Pat. No. 5,981,271 describes the process of outdoor thin-layer cultivation of algae in which the suspension of algae saturated with carbon dioxide and enriched with necessary nutrients, is distributed on inclined cultivation areas where the suspension of algae is distributed on inclined cultivation areas under turbulent flow, which depends on the velocity of flow, on the coefficient of the roughness of the cultivation surfaces, on the thickness of the algal suspension layer and the inclination of the cultivation surface. Between individual cultivation areas, carbon dioxide is supplied into the suspension and the suspension flowing from the lowest cultivation area is conveyed into the collecting tank from which it is pumped on the upper edge of the highest cultivation area. Bioreactor for accomplishing the mentioned process is composed of at least two individual cultivation meandering areas where the lower end of the upper area and the beginning of the next lower area, inclined in the opposite direction, are connected by channels in which outlets for the supply of carbon dioxide into suspension are placed.

U.S. Pat. No. 8,110,395 describes a photobioreactor system comprising: a plurality of interconnectable photobioreactor sections which, when connected together, form at least one longitudinally-oriented photobioreactor unit of the photobioreactor system, the photobioreactor sections each comprising a liquid flow channel, and a light-transparent cover that forms a gas headspace between the cover and the liquid flow channel, the cover being constructed and arranged to cover at least a substantial portion of the liquid flow channel and configured to provide the gas headspace even when a gas pressure within the photobioreactor unit is less than the atmospheric pressure surrounding the photobioreactor section, at least one photobioreactor unit of the photobioreactor system further including an evaporative cooling area, including a reservoir and a sprayer, the evaporative cooling area being disposed outside of the cover such that the reservoir is open to the atmosphere outside of the cover, the reservoir being in fluid communication with the liquid flow channel, the sprayer is configured to spray a liquid upwardly from within the reservoir.

U.S. Pat. No. 6,827,036 describes aquaculture apparatus comprising an elongated tube of flexible translucent material, the tube extending longitudinally along a tube site and having a lower section defining a watercourse, and a cover extending externally over the tube and being air-supported, said cover being at least partially spaced from the tube and providing an insulating space for insulating at least a substantial part of the tube.

U.S. patent application No. 20090130706 describes an enclosed photobioreactor configured to float on a body of water; the photobioreactor comprises: an elongated, longitudinally-oriented photobioreactor section constructed and arranged to contain a liquid medium comprising phototrophic organisms therein, the photobioreactor section comprises: a substantially flexible lower barrier comprising an upper surface in contact with and supporting the liquid medium; a cover constructed and arranged to cover the liquid medium within the photobioreactor section and further constructed and arranged to provide a gas headspace under the cover and above the liquid medium, the cover being at least partially transparent to light of a wavelength capable of driving photosynthesis; a first floatation element disposed on a first lateral side of the photobioreactor section; a second floatation element disposed on a second lateral side of the photobioreactor section; the first and second floatation elements being constructed and arranged to support the photobioreactor section for floatation on the body of water; and a plurality of tensioners constructed and arranged to apply tension to the lower barrier so as to maintain a substantial portion of the area of the lower barrier in a substantially horizontal configuration when the photobioreactor section is charged with the liquid medium, such that a continuous layer of the liquid medium has a substantially uniform depth which extends from approximately the first floatation element to approximately the second floatation element over at least a portion of the area of the lower barrier.

U.S. patent application No. 20100028976 describes a photobioreactor comprising: (a) a container adapted for holding fluid, comprising opposing first and second sidewalls, wherein at least one of the first and second sidewalls is transparent; (ii) opposing first and second end walls; (iii) a container bottom; and (iv) a container cover, wherein the first and second sidewalls comprise a plurality of separate sections, and wherein the separate sections are in fluid communication; (b) support struts for connecting the plurality of separate sections of the first and second sidewalls; (c) at least one inlet port in fluid communication with the container; (d) at least one outlet port in fluid communication with the container; (e) an aeration system in fluid communication with the container; and (f) a temperature control system connected to the container to control the temperature of the fluid within the container.

It should be noted that these US Patents and patent applications (including U.S. Pat. No. 5,981,271) do not solve construction problems of an elongated photobioreactor with the length of some tens of meters to some hundreds of meters and with small inclination regarding the horizontal plane, wherein such photobioreactor is provided with effective means for enhancement of heat and mass transfer between the liquid and gaseous mediums in it.

U.S. Pat. No. 9,938,492 describes a photobioreactor for cultivating and growing microalgae comprising: a sealed thin, visible light-conducting flexible plastic sheeting comprising an upper plastic sheeting panel and a lower plastic sheeting panel, the upper plastic sheeting panel and the lower plastic sheeting panel collectively forming a sealed tubular flat container, whereby one face of the lower plastic sheeting panel floats on the surface of a temperature modulating body of water and wherein the other face of the lower plastic sheeting panel is coated with microalgae within an aqueous medium forming a thin aqueous microalgae layer that is less than 1 cm in thickness; and where said upper plastic sheeting panel is held above the thin aqueous microalgae layer due to the slightly inflated airspace.

U.S. patent application No. 20210062124 describes at least one elongated photobioreactor, at a small angle relative to horizontal and mixed substantially or entirely by large bubble flow; this photobioreactor is used for contained cell culture, e.g., microalgae cultivation. Elongated, flexible, transparent, polymeric photobioreactor tubes, in near-grade and near-horizontal (e.g. sloped 1 degree to 3 degrees) orientation, and use of low-pressure air mixing, allow very inexpensive construction and operation. Multiple elongated tubes may be used for an independent operation of the multiple photobioreactor tubes for the same or different cells, e.g., microalgae and different applications. Low-pressure air is delivered near the low end of the bioreactor at less than 10 psi and without sparging, to produce large air bubbles that travel from the low end to the high end of the bioreactor, for turbulent mixing and gas exchange. Each inexpensive, flexible bioreactor tube is easily modified to improve internal flow characteristics and suspension of cells, and/or to include sensor and/or sampling collars and ports.

Attempts to solve these problems are presented in U.S. Pat. No. 8,986,985 and U.S. patent application No. 20200024558 to the author of these inventions and patent applications.

Reviews of technical problems connected with the design of industrial photobioreactors are presented in the articles: James C. Ogbonna, Hideo Tanaka "Industrial-size photobioreactors" CHEMTECH 1997, 27(7), 43-49. and O. Pulz "PHOTOBIOREACTORS: PRODUCTION SYSTEM FOR PHOTOTROPHIC MICROORGANISMS" Springer-Verlag, 2001.

It is known that temperature plays a very important role in the process of microalgae cultivation. It is detail analyzed in many articles and other materials.

It has been described, for example, in Monika Pawlita-Posmyk et al. "The influence of temperature on algal biomass growth for biogas production" MATEC Web of Conferences 240, 04008 (2018); Monique Ras et al. "Temperature effect on microalgae; a crucial factor for outdoor production" HAL Id: hal-00852286.

There are examples of optimal temperature conditions for algae cultivation of several microalgae species:

| | |
|---|---|
| *Haematococcus pluvialis* | 20° C.-28° C. |
| *Spirulina* | 30-35° C. |
| *Chlorella thermophila* (HTA1-65) | 33.0° C. |
| *Chlorella vulgaris* | 25-28° C. |
| *Chlorella mirabilis* | 10.1-20.5° C. |
| *Chlorella* sp. | 37.5° C. |
| *Chlorella marinahlorella pyrenoidosa* | 37.5° C. |
| *Chlorella vulgaris* | 27-30° C. |
| *Chlorella* | 27.0° C. |

This invention proposes a further modification of the technical solutions described in U.S. Pat. No. 8,986,985 and U.S. patent application No. 20200024558 of one of the authors.

It is the aim of this modification to provide the photobioreactor described in U.S. patent application No. 20200024558 a new feature: thermal control of a transparent flat duct applied for microalgae cultivation with keeping the other positive features described in U.S. patent application No. 20200024558.

SUMMARY OF THE INVENTION

A photobioreactor of this invention is constructed from several main elements.

There are two parallel posts' rows and two parallel rows of inclined supporting angles, which are installed on these posts. These posts and supporting angles form a supporting structure with the preset inclination angle, preferably, in the range of 0.1 degree/2. degree.

This supporting structure includes as well a bank of frames with fastened in them wire nettings: the frames are mutually abutted and are positioned in line with the small inclination to the horizontal plane.

In another version, each frame may be provided with a set of parallel rods instead of the wire netting.

Each frame is fabricated from two longitudinal Z-profiles and two transverse strips. It is possible to apply other profiles with upper horizontal shelves instead of Z-profiles: angles, C-channels, U-channels, and I-beams.

In another version, the wire netting can be substituted by a bank of parallel rods installed on the bottom shelves of the Z-profiles or the transverse strips of the frame.

In addition, there is a thermo-insulating plate (or some thermo-insulating plates) from a foamed plastic preferably of a white color, which is arranged on each wire netting. In addition, strips from the foamed plastic can thermo-insulate the internal surfaces of the middle sections of the Z-profiles.

There is a variable air pressure mattress(es), which is provided with inlet and outlet connections. This variable air pressure mattress is preferably made from a transparent or translucent flexible polymer. In addition, this variable air pressure mattress may be provided with channels for the passage of cooling or heating liquids (mainly—water).

In another version, the variable air pressure mattress is fabricated from white polymer film with a high reflecting coefficient in the visible range of the spectrum.

An inflatable sleeve from the transparent flexible polymer is situated on the frames and is supported underneath by the frames' wire nettings, the plates from foamed plastic, and the variable air pressure mattress. Each terminal section of the sleeve is provided with a port. These ports are formed in the inflatable sleeve by welding.

There is an inflatable mattress(es) from transparent or translucent polymer, which is provided with at least one inlet-outlet connection. This inflatable mattress serves for thermal insulation from above a flat duct ((a duct with a high value of ratio its width to its height) formed by the inflatable sleeve.

There is a bank of glass panes, which are mutually abutted and positioned in-line on the upper shelves of the Z-profiles of the frames (excluding the terminally positioned frames) and fastened on the upper shelves by fasteners, for example, by spring clips. The glass panes are fabricated preferably from UV-blocking glass.

These glass panes play several functions: protection of the inflatable mattress and the polymer sleeve against destruction by UV components of solar radiation and from hail. In addition, the glass panes allow easier cleaning of the upper surfaces of the photobioreactor from dust.

In addition, the glass panes in combination with the frames' wire nettings, the plates from foamed plastic, the variable air pressure mattress, and the inflatable mattress form the substantially flat duct in the inflated polymer sleeve intended for the combined flow of thin layer of microalgae suspension (broth) and gaseous medium with $CO_2$ component.

In such a way, the variable air pressure mattress serves for mixing a layer of microalgae suspension flowing with a gaseous medium containing $CO2$ in the flat duct formed by the inflatable polymer sleeve.

In addition, if the variable air pressure mattress is provided with the channels for the passage of a cooling or heating liquid, then this variable air pressure mattress serves too for thermal control of the broth's layer flowing in the formed flat duct of the inflated polymer sleeve.

If another method of mixing the microalgae suspension layer is used, the variable air pressure mattress with the channels for passage of cooling or heating liquid may be used without engaging its channels for variable air pressure and only for thermal control of the microalgae suspension.

The glass panes can be substituted by transparent (or translucent) polymer sheets.

Pressures in the channels of the variable air pressure mattress and the inflatable mattress are higher than the pressure in the inflatable sleeve; it ensures tight thermal and mechanical contact of the channels of the variable air pressure mattress with the inflatable sleeve and sufficient thermal insulating characteristics of the inflatable mattress.

It should be noted that for substantially long closed photobioreactors their average operation pressure of gaseous medium can significantly exceed the hydraulic pressure of a thin layer of microalgae suspension.

This causes a cylindrical-wise inflated shape of the polymer sleeve and, therefore, a segment-wise shape of the thin layer of microalgae suspension flowing on the bottom of the polymer sleeve. Application of the glass panes prevents this phenomenon.

As it was noted, the terminal sections of the polymer sleeve are provided with inlet and outlet ports in the case of gas-liquid co-current flow in the flat duct, or with inlet-outlet ports in the case of gas-liquid counter flow in the flat duct formed by the inflated polymer sleeve.

The angles of inclination of the supporting structure can vary along the flat duct formed by the inflated polymer sleeve.

In particular, these angles of inclination may be of relatively small values for the proximal sections of the flat duct (regarding the flow direction of the microalgae suspension) with gradually increasing the inclination angles at the middle and distal sections of the flat duct. It allows choosing an optimal change of the microalgae suspension depth along the whole length of the flat duct.

The frame situated last downstream can be designed with adjustable inclination playing in such a manner a function of an adjustable weir, which regulates the height of microalgae suspension in the flat duct.

The inlet and outlet ports are in fluid communication with two headers, which serve for the supply of the air or gaseous medium enriched with $CO_2$ into the internal space of the flat duct and remove the air or the gaseous medium from the internal space of the flat duct. In addition, these ports serve for the supply of suspension of microalgae or cyanobacteria into the internal space of the flat duct and withdrawal of suspension of microalgae or cyanobacteria from this internal space.

The header, which serves to supply the microalgae suspension into the flat duct, can be provided with a level gauge ensuring control of an optimal flow rate of the microalgae suspension, i.e., it ensures the combined flow of microalgae suspension and gaseous medium containing CO2 in the flat duct of the inflated sleeve within their optimal ratio.

Air or a gaseous medium with $CO_2$ supplied into the proximal header (regarding the flow direction of the gaseous medium) can be previously cooled and/or dried; it allows the establishment of the optimal temperature of the microalgae suspension along the flat duct.

However, these measures are not sufficient in many cases because heat is generated in the microalgae broth by absorbed solar radiation and heat, which is transferred into the inflatable sleeve from the environment (or loosed from it to the environment).

It should be noted, that the elongated flexible polymer sleeve, which forms the flat duct, is functioning as a flexible elastic membrane. Such flexible membrane vibrates in response to the pulsation of the pressure of the gaseous medium flow with the enhancement of heat and mass transfer between the gaseous medium and the thin layer of microalgae suspension.

The application of this effect in heat exchangers is described in the article: by Yanhua Lu et al. ENHANCED PERFORMANCE OF HEAT RECOVERY BY AIR-INDUCED FILM VIBRATION, International Journal of Thermal Science, 49, July 2010 pp. 2037/2041.

In this case, the variable air pressure mattress may be used only for thermal control of flowing microalgae suspension.

The variable air pressure mattress can be fabricated from transparent or translucent polymer film. This allows utilizing as well solar radiation reflected from below by the plates of the white foamed plastic onto the flat duct through the variable air pressure mattress.

The supporting angles can be provided with aligning screws to minimize misalignment of the frames with the wire nettings and to achieve even distribution of the microalgae suspension across the width of the flat duct.

A header that supplies microalgae suspension into the flat duct of the inflatable sleeve can be equipped with a heat exchanging unit for the establishment of an optimal temperature of the microalgae suspension.

In addition, some temperature sensors can be placed between the variable air pressure mattress and the inflated polymer sleeve to provide temperature data regarding the microalgae suspension and to perform regulation of this temperature. These temperature sensors are preferably thermo-insulated from their undersides.

The proposed photobioreactor comprises auxiliary equipment: fans (or blowers), pumps, and a control unit, which regulates the functioning of this auxiliary equipment.

DESCRIPTION OF PREFERABLE EMBODIMENTS

Figure 1:
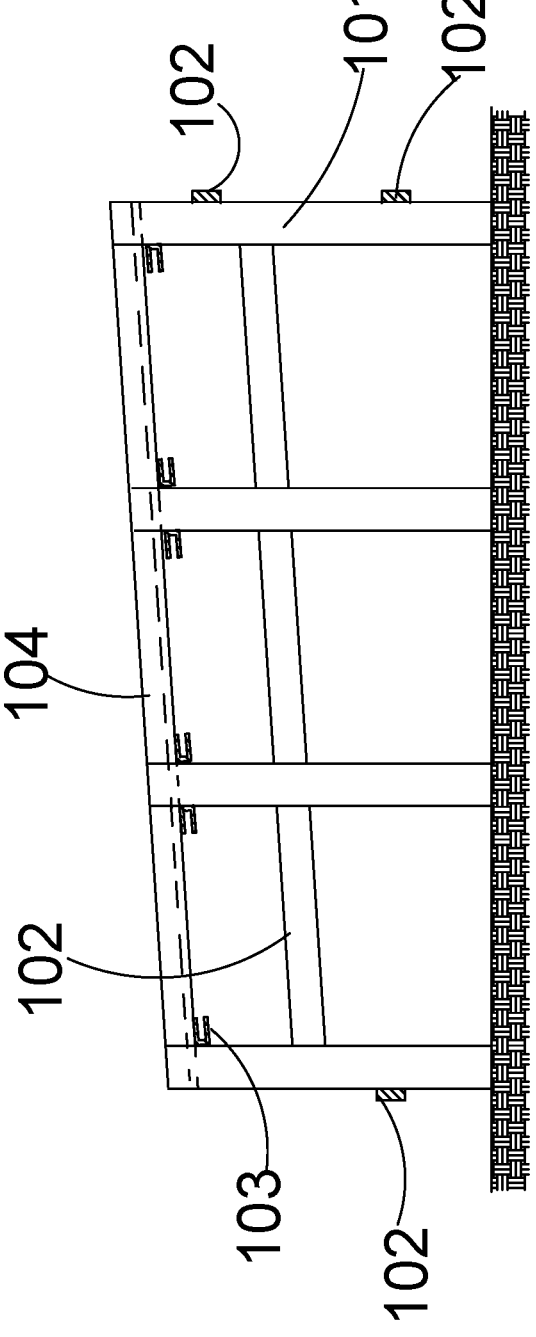
FIG. 1 demonstrates a side view of supporting angles installed on posts.

FIG. 1 demonstrates a side view of supporting angles installed on posts. It comprises posts 101 with cross-bars 102; a supporting angle 103 and transverse channel bars 104.

Figure 2A:
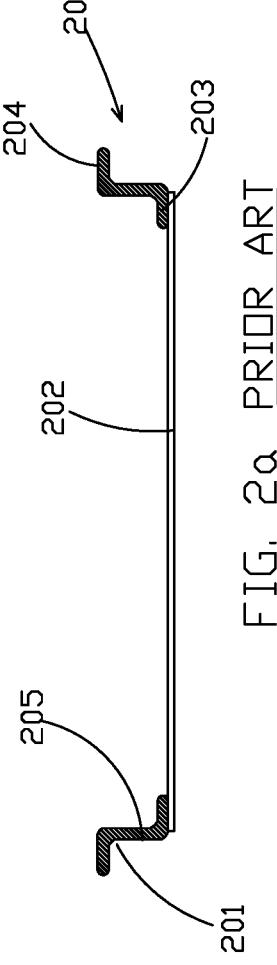
FIG. 2a and FIG. 2b show elevation and cross-section views of a frame with Z-profiles used for the construction of the longitudinal sides of the frame.
Figure 2B:
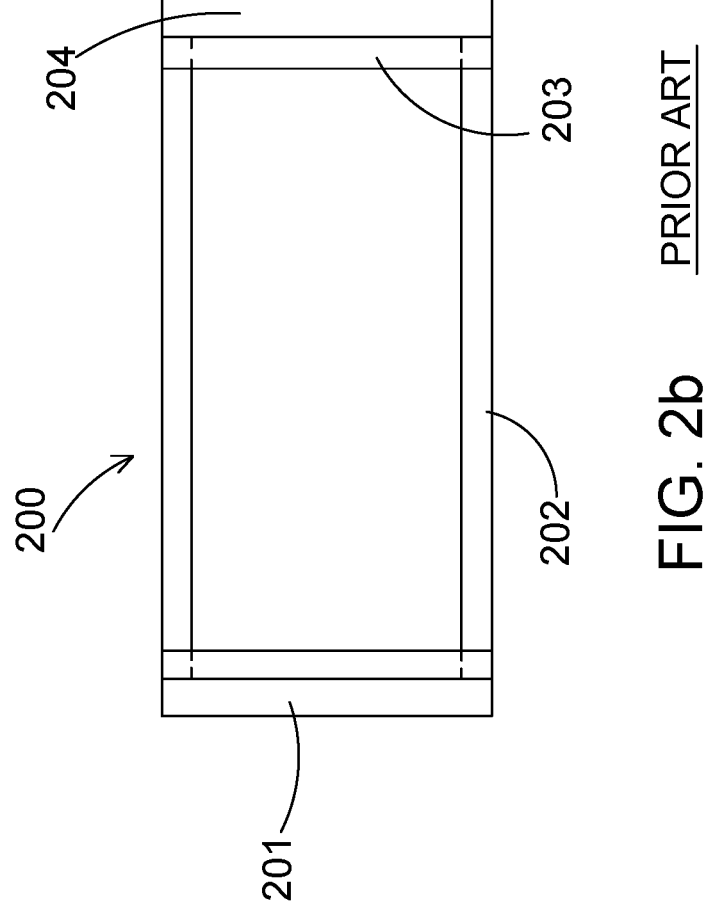

FIG. 2a and FIG. 2b shows cross-section and elevation views of frame 200 with Z-profiles, which are used for the construction of the longitudinal sides of frame 200.

Frame 200 comprises Z-profiles 201 and a transverse cross-bar 202.

Each Z-profile comprises a bottom shelf 203, an upper shelf 204 and a middle section 205.

Figure 2C:
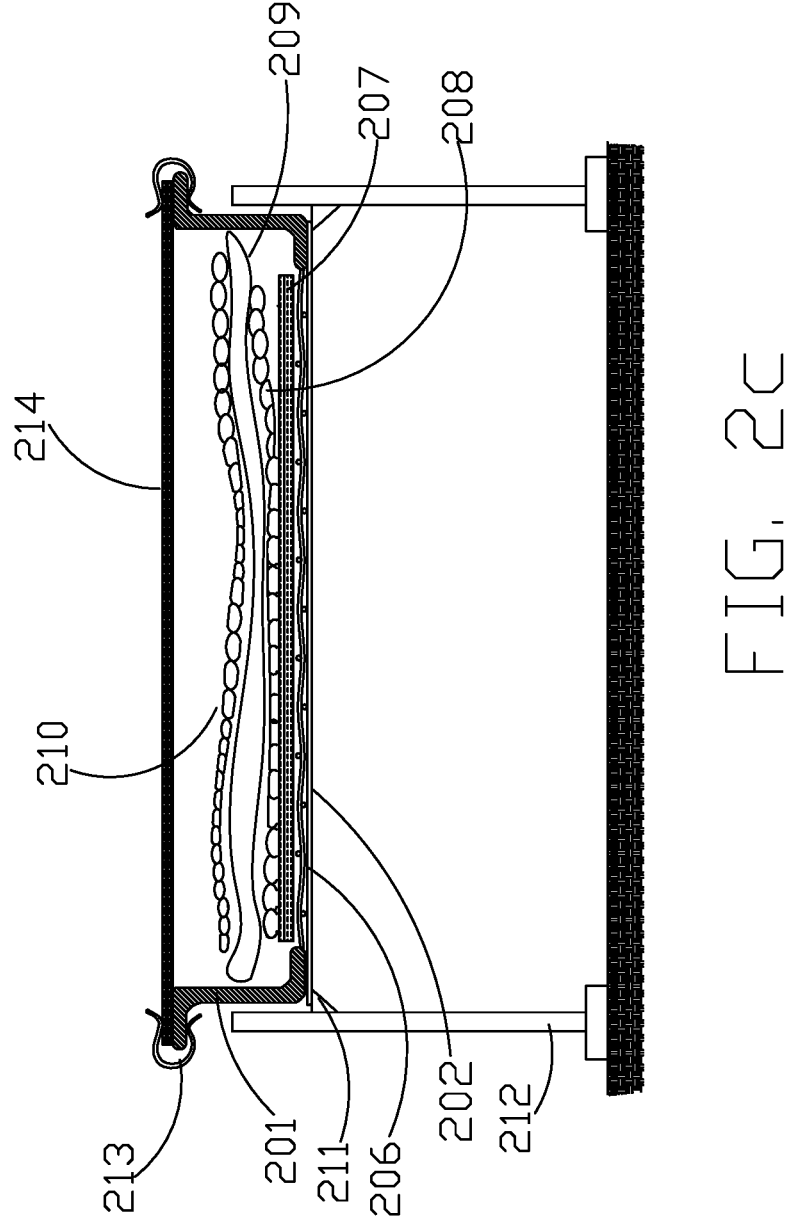
FIG. 2c shows a cross-section of the frame, which is fastened on posts; a wire netting; a plate from foamed plastic; a variable air pressure mattress in its non-operation condition; a non-inflated polymer sleeve; a non-inflated thermo-insulating transparent mattress.

FIG. 2c shows a cross-section of the frame, which is fastened on the posts with angles, with the wire netting, the plate from foamed plastic, the variable air pressure mattress in its non-operating condition, non-inflated polymer sleeve, and the thermo-insulating transparent mattress in its non-inflated condition.

It comprises frame 200 with Z-profiles 201 supported by angles 211 and posts 212, the transverse cross-bars 202, the wire netting 206 with plate 207 from foamed plastic, the variable air pressure mattress 208 in its non-inflated state and the non-inflated polymer sleeve 209, the non-inflated transparent mattress 210, the glass pane 214 and fasteners 213.

Figure 2D:
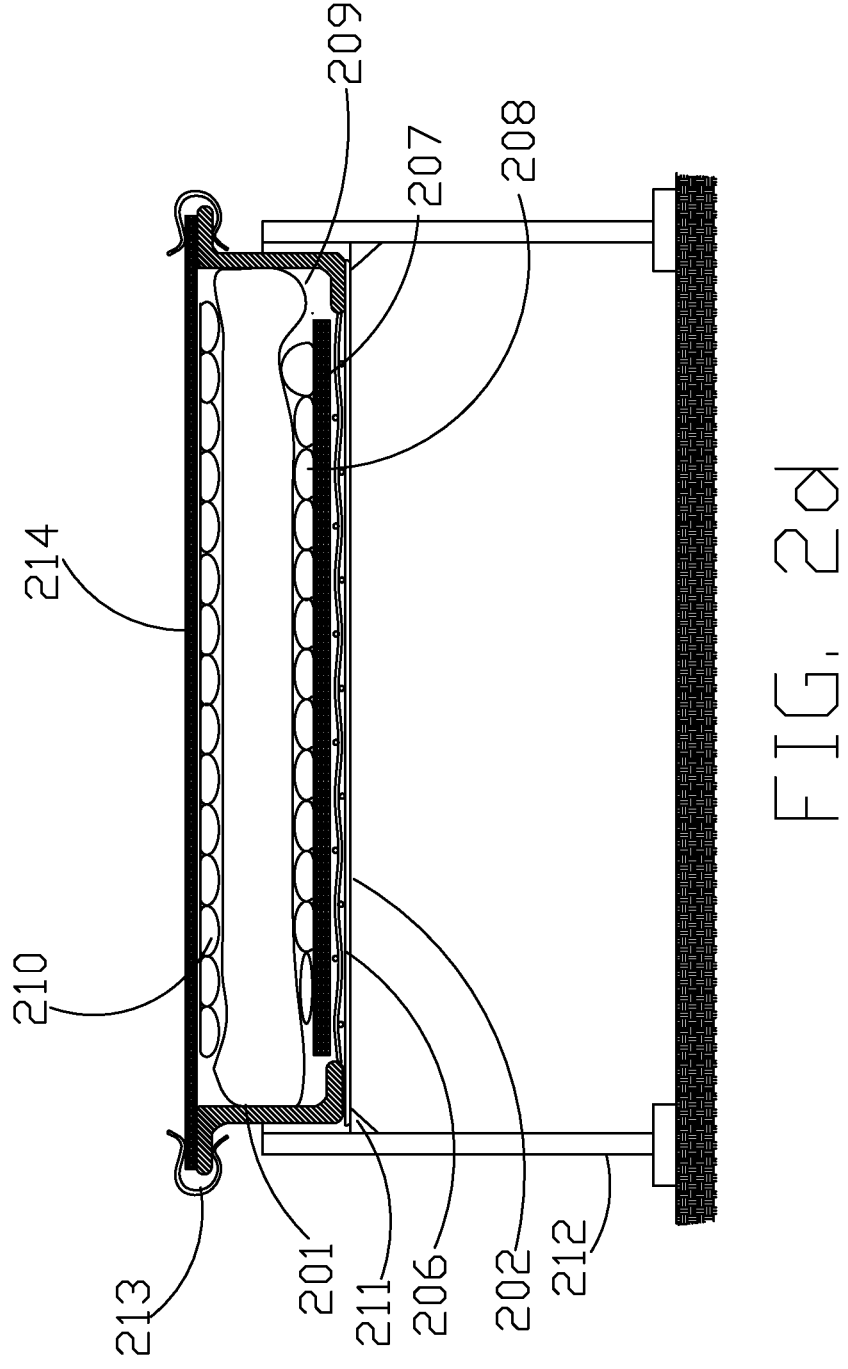
FIG. 2d shows a cross-section of the frame, which is fastened on the posts; the wire netting; the plate from foamed plastic; the variable air pressure mattress; the inflated polymer sleeve in the form of a flat duct; the inflated thermo-insulating transparent mattress.

FIG. 2d shows a cross-section of the photobioreactor with the inflated polymer sleeve.

It comprises Z-profiles 201, the transverse cross-bars 202, the wire netting 206, plate 207 from foamed plastic and the variable air pressure mattress 208, the inflated polymer sleeve 209, the inflated transparent mattress 210, a glass pane 214, supporting angles 211, posts 212 and fasteners 213.

Figure 3A:
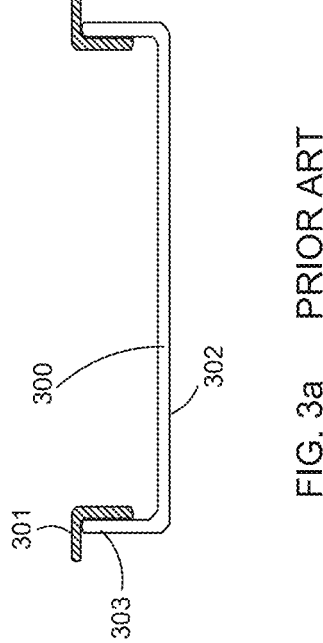
FIG. 3a shows a cross-section of a frame with the application of angle profiles for the construction of the longitudinal sides of the frame.

FIG. 3a shows a cross-section of frame 300 with the application of angle profiles for the construction of the longitudinal sides of frame 300.

It comprises longitudinal angle profile 301, which is bonded with strips 302 with bowed terminal sections 303.

Figure 3B:
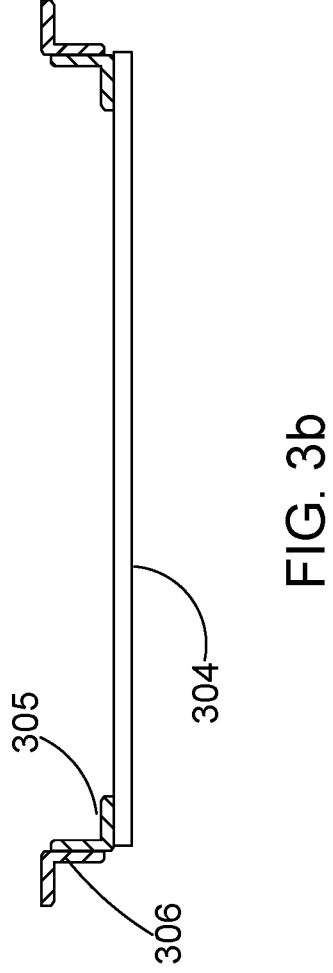
FIG. 3b shows a cross-section view of a frame with two angle profiles used for the construction of the longitudinal sides of the frame.

FIG. 3b shows a cross-section view of a frame with two angle profiles used for the construction of the longitudinal (lateral) sides of the frame.

It comprises a transverse cross-bar 304, first angle profiles 305, and second angle profiles 306.

Figure 4:
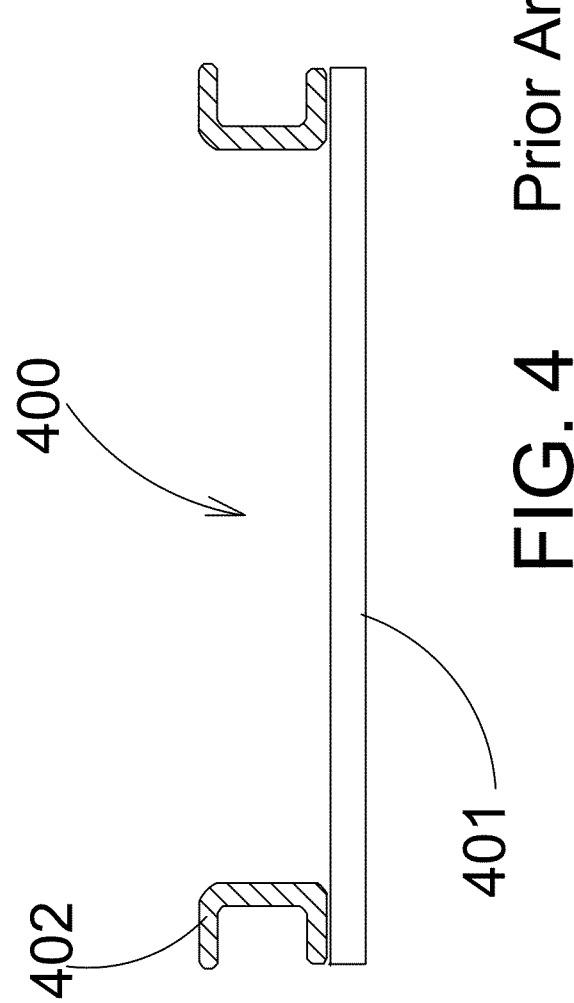
FIG. 4 shows a cross-section of a frame with the application of U-profiles for the construction of the longitudinal sides of the frame.

FIG. 4 shows a cross-section of frame 400 with the application of U-profiles for the construction of the longitudinal sides of frame 400. It comprises longitudinal U-profiles 402, which is joined with strip 401.

Figure 5:
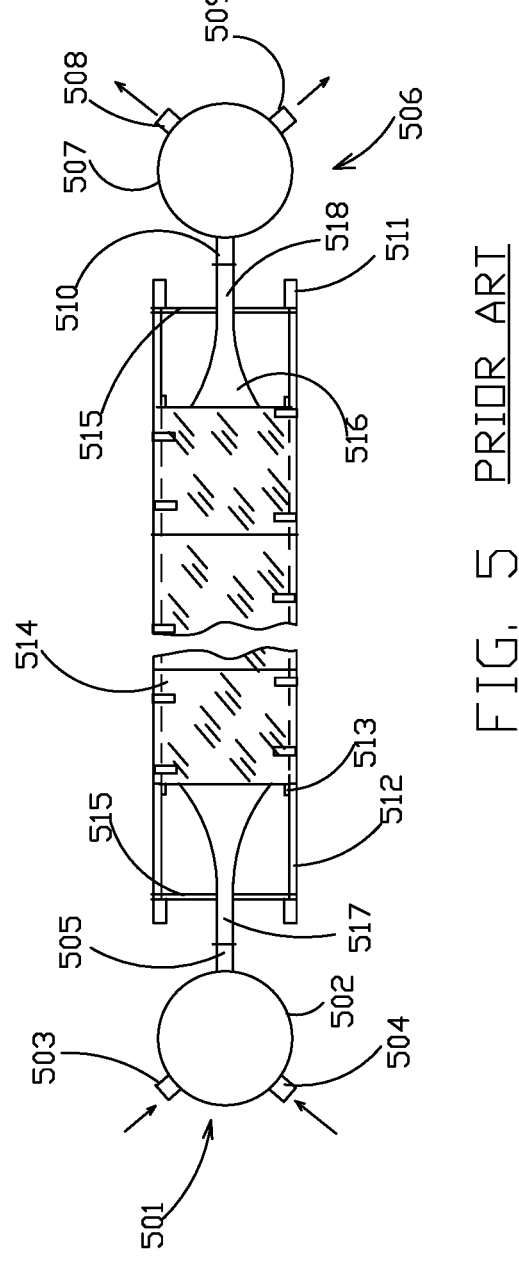
FIG. 5 shows an elevation view of the photobioreactor including two headers.

FIG. 5 shows an elevation view of a photobioreactor including two headers.

It comprises: header 501 with housing 502, a gas inlet connection 503, a broth (microalgae suspension) inlet connection 504, a gas-broth outlet port 505; header 506 with housing 507, an gas outlet connection 508, a broth outlet connection 509, an inlet gas-broth port 510; posts 511; supporting angles 512; Z-profiles 513 of non-terminal frames; glass panes 514; terminal frames 515; a polymer sleeve 516 with an inlet and outlet ports 517 and 518.

Figure 6:
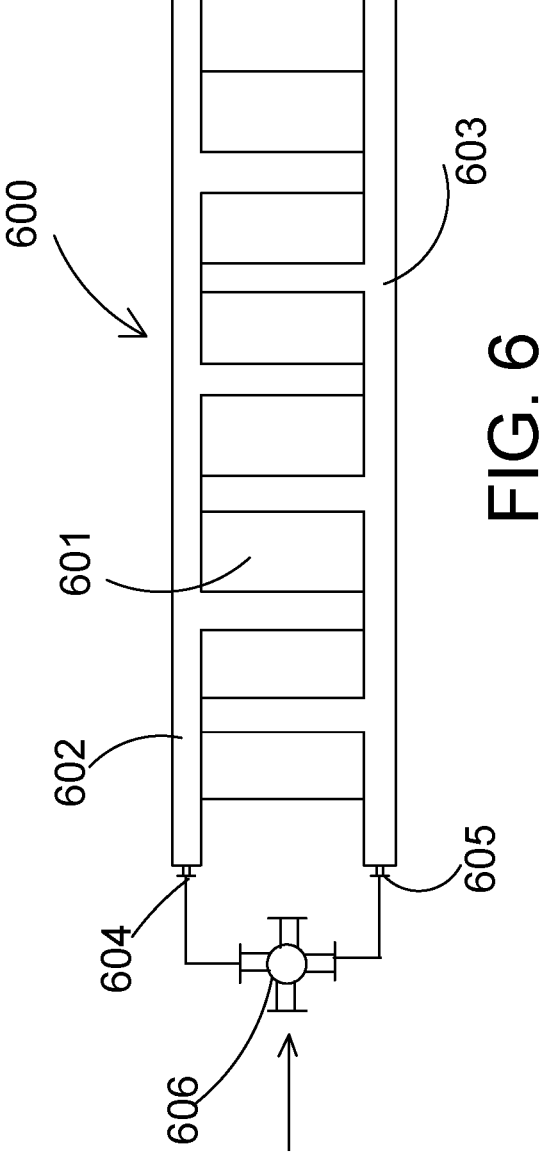
FIG. 6 shows an elevation view of the first version of a variable air pressure mattress.

FIG. 6 shows an elevation view of the first version of a variable air pressure mattress 600.

It comprises the variable air pressure mattress 600 itself with idle sections 601, alternatingly operating sections 602 and 603, inlet/outlet connections 604 and 605, and a four-way valve 606.

Figure 7:
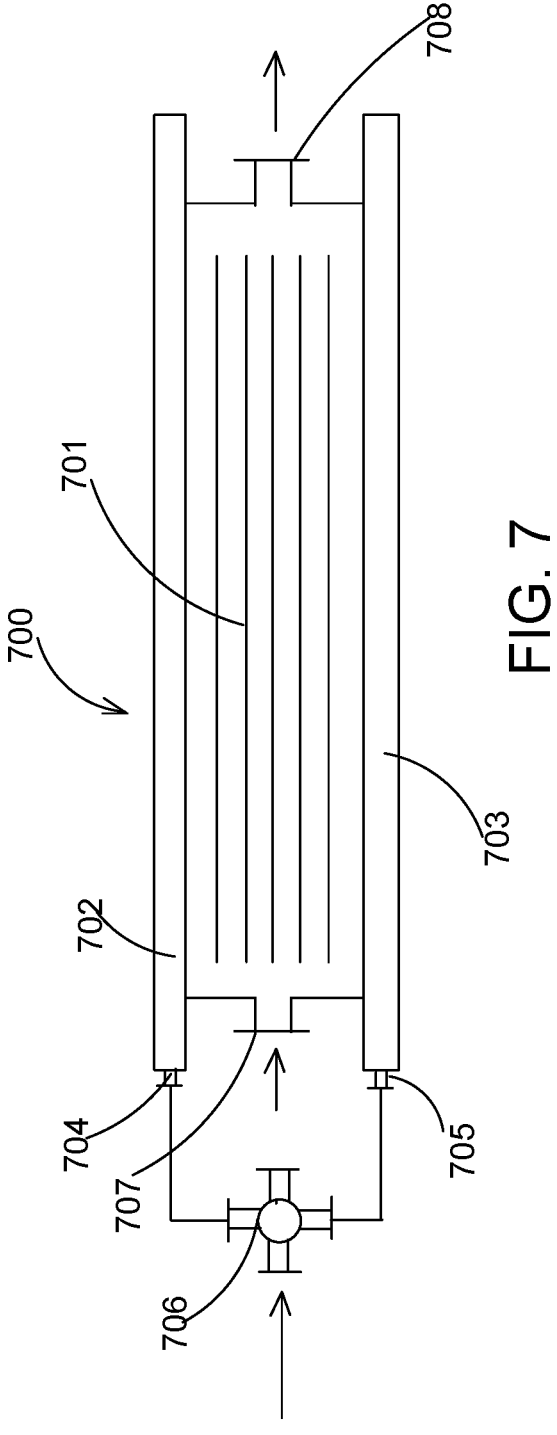
FIG. 7 shows an elevation view of the second version of a variable air pressure mattress, which includes a heat exchanging section.

FIG. 7 shows an elevation view of the second version of a variable air pressure mattress. It comprises the variable air pressure mattress 700 itself with heat exchanging section 701, alternatingly operating sections 702 and 703, inlet/outlet connections 704 and 705, a four-way valve 706, inlet and outlet connections 707 and 708 for supply and withdrawal of cooling or heating liquid medium.

Figure 8:
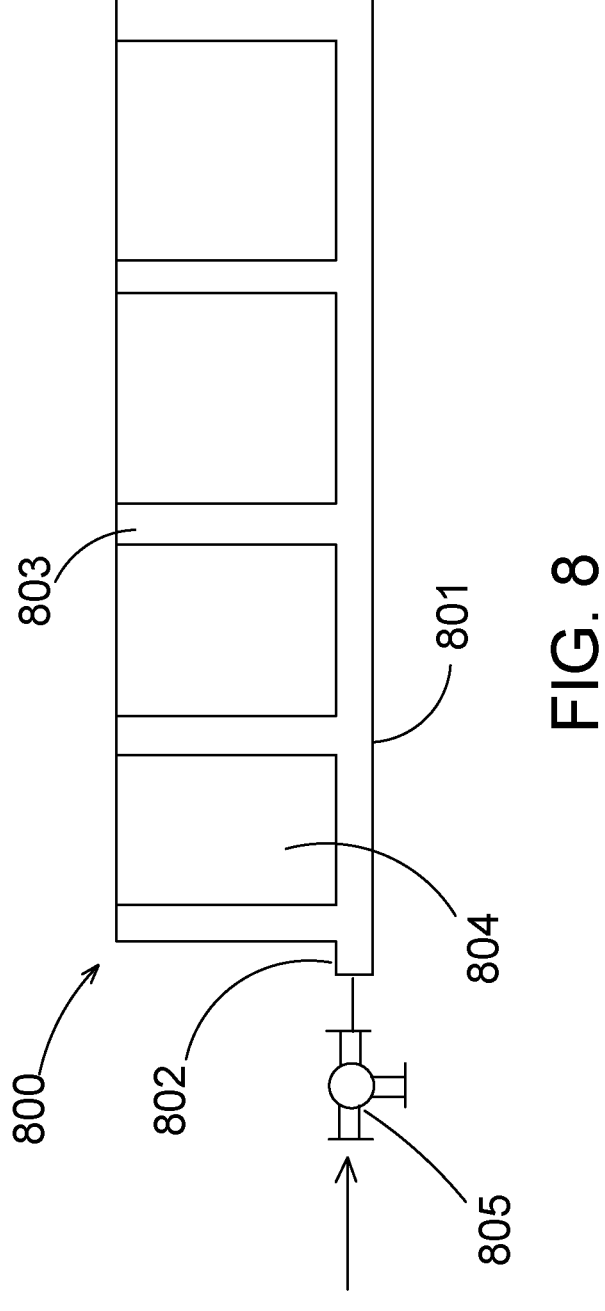
FIG. 8 shows an elevation view of a variable air pressure mattress designed as a comb structure, wherein its inflatable sections are separated by idle sections, and pulsating pressurized air is supplied into the variable air pressure mattress via a 3-way valve.

FIG. 8 shows an elevation view of a variable air pressure mattress designed as a comb structure, wherein inflatable sections are separated by idle sections, and pressurized air is supplied into the variable air pressure mattress via a 3-way valve.

It shows the variable air pressure mattress 800 itself with header 801, an inlet/outlet connection 802, inflatable sections 803, idle sections 804, and 3-way valve 805.

Figure 9:
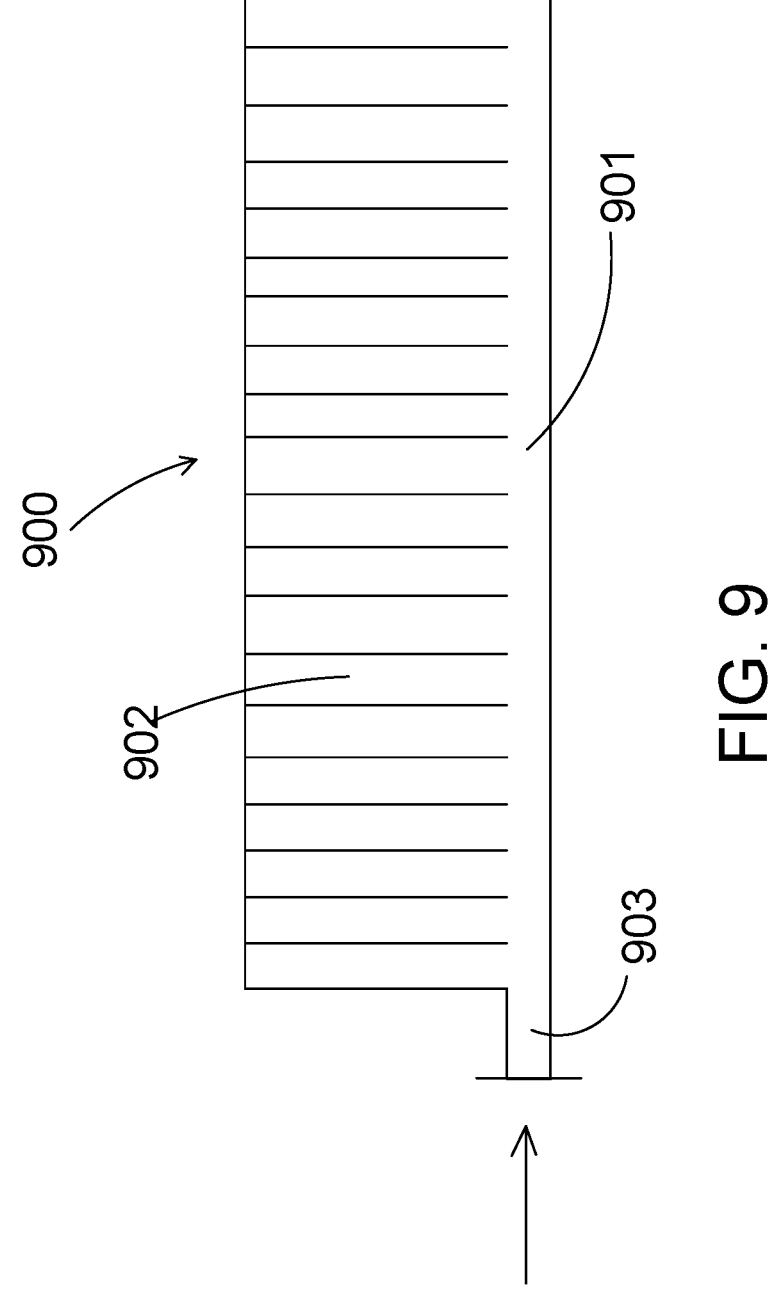
FIG. 9 shows an elevation view of an inflatable transparent mattress for thermo-insulating the inflated polymer sleeve from above.

FIG. 9 shows an elevation view of an inflatable mattress for thermo-insulating the inflated polymer transparent or translucent sleeve from above.

It comprises the inflatable mattress 900 itself with a header section 901, inflatable channels 902, and an inlet/outlet connection 903.

The invention claimed is:

1. A photobioreactor for cultivation of microalgae or cyanobacteria comprising a support structure with two parallel rows of posts and supporting inclined angles profiles installed on said posts; said supporting inclined angle profiles support a bank of abutted in-line frames, wherein each said abutted inline frame is equipped with wire nettings, two longitudinal Z-profiles and two transverse cross-bar and wherein there are transparent or translucent glass panes fastened on the upper shelves of said Z-profiles; a bank of following longitudinal elements sandwiched between said frames and said transparent or translucent glass panes in the following order:: said bank of abutted in-line frames provided with wire nettings, plates of foamed plastic, above said frames, a variable air pressure mattress or mattresses above said foamed plastic plates which are configured to prevent mechanical abrasion to the said variable air pressure mattress, an inflatable transparent or translucent sleeve above said variable air pressure mattress, an inflatable mattress in its inflated state above said inflatable transparent or translucent sleeve, and said glass panes on top of said inflatable mattress; wherein said inflatable transparent or translucent polymer sleeve includes inlet and outlet ports and wherein said inflatable transparent or translucent polymer sleeve forms in its inflated state a flat duct, which is inclined at an angle determined by the inclination of said abutted frames; and wherein said support structure includes two parallel rows of said posts and two parallel rows of said inclined supporting angles secured to said posts, and wherein said angles support said bank of said abutted in-line frames; and wherein said flat duct of said inflatable transparent or translucent polymeric sleeve is in fluid communication with first and second headers via said inlet and outlet ports for supplying and removing culturing media and gaseous medium containing carbon dioxide into and out of said flat duct; said photobioreactor for cultivation of microalgae or cyanobacteria is operating in the following manner: diluted suspension of microalgae or cyanobacteria is entering into said inlet port and flows as a thin layer in said flat duct and is removed from said flat duct via said outlet port; gaseous medium containing carbon dioxide is entering into said inlet port and flows in said flat duct above said thin layer of suspension of microalgae or cyanobacteria and are removed from said duct via said outlet port.

2. The photobioreactor as claimed in claim 1, wherein the first header further includes a level gauge and a controller for monitoring the level of microalgae suspension within said photobioreactor.

3. The photobioreactor as claimed in claim 1, wherein the frames and the supporting angles include aligning screws for preventing misalignment of said frames.

4. The photobioreactor as claimed in claim 1, wherein the first header supplies the microalgae suspension into the flat duct by the inlet port and wherein the second header supplies the gaseous medium with carbon dioxide into said flat duct via the outlet port, wherein the suspension and the gaseous medium flow in opposite directions in the flat duct, with the inlet and outlet ports being interchangeable depending on the desired direction of flow.

5. The photobioreactor as claimed in claim 1, wherein the angle of inclination of said supporting angles is gradually increasing along the direction of flow of the microalgae suspension in the flat duct.

6. The photobioreactor as claimed in claim 1, wherein supply of the gaseous medium into the flat duct from the first or second header is applied with pulsating pressure at the header.

7. The photobioreactor as claimed in claim 1, wherein the variable air pressure mattress is configured with a section comprising channels for passage of a cooling or heating liquid, separate from the channels that inflate the mattress, and wherein said variable air pressure mattress is provided with inlet and outlet connections for supply and withdrawal of said cooling or heating liquid.

8. The photobioreactor as claimed in claim 7, wherein the operating pressure of the cooling or heating liquid in the variable air pressure mattress is higher than the operating pressure of the gaseous medium containing carbon dioxide in the inflatable sleeve, wherein the differential pressure is configured to enhance the stability and integrity of the inflatable sleeve during operation.

9. The photobioreactor as claimed in claim 1, wherein the variable air pressure mattress is fabricated from transparent or translucent polymer and the plates from white coloured foamed plastic to reflect light passing through the sleeve and mattress.

10. The photobioreactor as claimed in claim 1, wherein one or more temperature sensors are placed between the variable air pressure mattress and the inflatable transparent or translucent sleeve, said temperature sensors being configured to monitor and regulate the temperature of the microalgae suspension, thereby ensuring optimal growth conditions.

11. The photobioreactor as claimed in claim 1, wherein the photobioreactor comprises auxiliary equipment further comprising of pumps for pumping the microalgae suspension, either fans or blowers for the supply of the gaseous medium containing carbon dioxide, either 4-way valves or 3-way valves, and a control unit, wherein these components are configured to interact with the inflatable sleeve which conducts the microalgae suspension, enhancing the controlled environment for optimized growth condition.

12. The photobioreactor as claimed in claim 1, wherein the operating pressures of air in the variable air pressure mattress or mattresses and the inflatable mattress are higher than the operating pressure of the gaseous medium containing carbon dioxide in the inflatable sleeve, wherein the differential pressure is configured to enhance the stability and integrity of the inflatable sleeve during operation.

13. The photobioreactor as claimed in claim 1, wherein the variable air pressure mattress is fabricated from white polymer film with a high reflection coefficient in the visible range of the spectrum, configured to reflect light and optimize light distribution for microalgae cultivation.

14. The photobioreactor as claimed in claim 1, wherein the variable air pressure mattress is designed as a comb structure, its inflatable sections are separated by idle sections, and wherein pressurized air is supplied into said variable air pressure mattress via a 3-way valve, the comb structure being configured to enhance mixing and distribution of the microalgae suspension.

15. The photobioreactor as claimed in claim 1, wherein the frame situated last downstream comprises an adjustable inclination configured to operate as an adjustable weir, thereby regulating the height of the microalgae suspension in the flat duct.

* * * * *